United States Patent [19]

Loedding et al.

[11] Patent Number: 5,156,776
[45] Date of Patent: Oct. 20, 1992

[54] AEROSOL GENERATING SYSTEM

[75] Inventors: Hubert Loedding, Lehrte; Horst Windt, Burgwedel; Wolfgang Koch, Steimbke; Randolf Klingebiel, Hanover, all of Fed. Rep. of Germany; Richard White, Bourg en Bresse, France

[73] Assignees: Solvay Deutschland GmbH, Hanover; Fraunhofer-Gesellschaft zur Foerderung dur angewandten Forschung e.V., Munich, both of Fed. Rep. of Germany

[21] Appl. No.: 820,081

[22] Filed: Jan. 13, 1992

[30] Foreign Application Priority Data

Oct. 19, 1991 [DE] Fed. Rep. of Germany ....... 4134665

[51] Int. Cl.$^5$ ................................................ B01F 3/04
[52] U.S. Cl. ..................... 261/27; 261/78.2; 261/55; 261/36.1; 128/203.25; 128/203.12
[58] Field of Search ................. 261/78.2, 27, 55, 36.1; 128/203.25, 204.22, 203.12, 203.14

[56] References Cited

U.S. PATENT DOCUMENTS

| | | | |
|---|---|---|---|
| 4,471,773 | 9/1984 | Bunnell et al. | 128/204.21 |
| 4,611,590 | 9/1986 | Ryschka et al. | 128/203.14 |
| 4,629,478 | 12/1986 | Brower et al. | 261/78.2 |
| 4,905,685 | 3/1990 | Olsson et al. | 128/203.12 |
| 5,030,253 | 7/1991 | Tokuhiro et al. | 261/78.2 |

Primary Examiner—Tim Miles
Attorney, Agent, or Firm—Foley & Lardner

[57] ABSTRACT

An aerosol generator useful as an atomizer for controllably and reproducibly producing wet or dry aerosols for inhalation studies, including a nebulizer for producing an aerosol from a liquid and an air stream, a liquid dosing device such as a step dosing pump for controllably feeding a liquid to be atomized to the neubilizer, an apparatus such as a mass flow controller for regulating the flow of an air stream to the nebulizer to provide an amount needed to atomize the liquid, and optionally to dilute the resulting aerosol, a conduit for conveying the aerosol formed in the nebulizer to an aerosol exposure chamber, a measuring device such as a light-scattering diffusion photometer into which a sample of the aerosol is introduced for determining the concentration of the aerosol, and a control unit for controlling the liquid supply device and the adjustable air supply to produce an aerosol having a predetermined desired concentration; the control unit being operated either manually or by a computer responsive to measured values determined by the measuring device.

21 Claims, 5 Drawing Sheets

MASS (%)

MMAD : 0.72 (μm)
geom. S. dev.: 1.61

AERODYN. DIAMETER (μm)

FIG. 4(a)

(%) CUMULATIVE

AERODYN. DIAMETER (μm)

BMRC . 80.01 (%)
ACGIH . 82.00 (%)

FIG. 4(b)

AEROSOL GENERATING SYSTEM

BACKGROUND OF THE INVENTION

The present invention relates to an apparatus for producing an aerosol from a liquid.

Medical inhalation devices are known and are commercially available for treating diseases and/or irritations of the respiratory tract and for performing controlled clinical trials. Typically, such devices form aerosols by dispersing liquids by means of compressed air or ultrasonic nebulization. Known medical aerosol generators are subject to the disadvantages that 1) the concentration of the aerosol can be adjusted only within very narrow limits ($\pm 20\%$), if at all;
2) the concentration of the aerosol is not monitored;
3) comparatively large amounts of a substance, usually at least several milliliters, are needed for the devices to operate properly to produce aerosols;
4) liquids that tend to foam or froth cannot be atomized; and
5) the concentration of the resulting aerosol tends to vary over time.

These disadvantages are serious and render such inhalators inadequate for use as atomizers for research purposes, e.g. for determining effective dosages of pharmacologically active substances, for specific provocation of the airways with various irritants, or for activity studies on drugs administered by inhalation.

Compounds synthesized for research purposes are often very expensive and frequently are available only in small amounts. Commercially available atomizers require comparatively large amounts of material to produce aerosols and are not suitable for producing uniform aerosols from very small amounts of substances.

SUMMARY OF THE INVENTION

It is the object of the invention to provide an aerosol generator which overcomes the disadvantages of the prior art.

Another object of the invention is to provide an aerosol generator which can produce a controlled aerosol from a relatively small amount of a test material.

A further object of the invention is to provide an aerosol generator which enables the concentration of the resulting aerosol to be continuously monitored.

It is also an object of the invention to provide an aerosol generator which can maintain an essentially constant aerosol concentration in an aerosol chamber over a period of time.

Yet another object of the invention is to provide an aerosol generator which can successfully produce aerosols from substances which tend to froth or foam.

An additional object of the invention is to provide an aerosol generator which is controllably adjustable to provide aerosols over a wide range of concentrations.

A still further object of the invention is to provide an aerosol generator which can be used to study pulmonary functions.

Another object of the invention is to provide an aerosol generator which can be used to administer precise aerosol dosages of pharmacologically active substances to animals in order to determine effective dosages of the pharmacologically active substances or to examine toxic effects of inhaled compounds on pulmonary mechanics.

It is also an object of the invention to provide an aerosol generator which can provide calibrated results so that tests run in different laboratories or tests run in the same laboratory at different times can be compared.

It is also an object of the invention to provide an aerosol generator which enables an experimenter to perform pulmonary function tests during aerosol delivery.

A further object of the invention is to provide an adjustable aerosol generator which is compact in size and which is flexible, convenient and easy to use.

A particular object of the invention is to provide an aerosol generator which enables use of aerosol test protocols in inhalation tests requiring administration of precise concentrations of active substances for predetermined times in a reproducible manner.

These and other objects of the invention are achieved by providing an aerosol generator comprising, in combination, a nebulizer for producing an aerosol from a liquid and an air stream; a device for adjustably supplying a controlled amount of a liquid from which an aerosol is to be generated to the nebulizer; an adjustable air source for supplying a controlled air stream to the nebulizer; a liquid discharge communicating with the nebulizer for discharging excess liquid from the nebulizer; an aerosol conduit leading from the nebulizer; an air flow meter for measuring the amount of air supplied by the air supply; a timer operatively connected to the liquid supply device and to the air source for controlling the duration of aerosol generation; and a detector for measuring the concentration of an aerosol discharged from the aerosol conduit.

The aerosol conduit may discharge into an optional aerosol exposure chamber so that an aerosol generated in the nebulizer will be conveyed to the aerosol exposure chamber. Alternatively, the aerosol conduit may discharge into a plethysmograph adapted to accept and release aerosols.

In accordance with a particularly preferred aspect of the invention, the aerosol generator further comprises a dilution air line leading from the adjustable air source to the aerosol conduit, and the air source supplies a second controlled air stream to the dilution air line to facilitate controlled dilution of the aerosol from the nebulizer.

The liquid supply device, e. g. a step dosing pump, takes the liquid to be atomized either from a supply reservoir, a syringe, or a soft ampoule and feeds controlled amounts of liquid through a line to the nebulizer. The adjustable air source delivers a controlled air stream to the nebulizer via a suitable duct system. The liquid supply device and the adjustable air source form an integrated unit. The nebulizer is a pneumatic atomizer configured such that the liquid to be atomized is dispersed as droplets which are picked up by the air stream and conveyed away through the aerosol conduit. The aerosol may be conveyed to an aerosol exposure chamber or to plethysmograph adapted to accept and release aerosols. If desired, the discharge line from the nebulizer may form a closed circuit with the liquid supply device and may optionally return any undispersed liquid to the supply reservoir. A second air stream may be introduced into the aerosol conduit to dilute the aerosol. A sample is diverted from the aerosol stream after it leaves the atomizer and is fed to the measuring device, which is a particle detector which determines the aerosol concentration. Desirably, a computer regulates the liquid supply device and the adjustable air source in response to the values measured by the detector to produce an aerosol having a controlled concentration.

In accordance with the invention a liquid is withdrawn from a suitable supply container by means of a liquid dosing device, and the liquid and the amount of air needed to form an aerosol are fed through separate conduits to the atomizer. The aerosol stream may, in accordance with the invention, be diluted with additional air. The resulting aerosol stream is conveyed to an aerosol exposure chamber or to a plethysmograph adapted to accept and release aerosols. A part of the aerosol stream is conducted, either through a diversion line leading from the aerosol conduit or through a measurement sample line leading from the aerosol exposure chamber, to a measuring device for measuring the concentration of the aerosol. In an advantageous embodiment any undispersed liquid is returned from the nebulizer through a return line to the liquid supply container.

The inhalation system according to the invention accordingly combines several functions into a single system. It includes a dosing device, preferably comprising a microdosing pump, for supplying controlled amounts of liquid from which an aerosol is to be formed, and a nebulizer in which the liquid is atomized with a stream of air to form an aerosol. In a preferred embodiment, the system also includes a dilution line for introducing a second air stream into the aerosol stream leaving the nebulizer to achieve a controlled dilution. According to the invention this entire system can be controlled automatically to carry out a desired, predetermined test program.

Advantageously, both the liquid to be atomized and the amount of air needed for atomization and possible dilution, i.e., the additional air, are regulated automatically in accordance with a predetermined program. The liquid dosing preferably is performed by means of a microdosing pump driven by a stepping motor. This pump can draw the liquid either from a supply reservoir, from a syringe (for small amounts to be atomized), or from a soft ampoule (for sterile conditions), so that for medical applications the proper handling of the liquid is assured. The liquid is fed forcibly to an atomizer. In this manner the ratio between the mass flow of the liquid and the mass flow of the air stream which picks up the liquid can be varied over a wide range. If dry aerosols are to be formed from solid substances which are dissolved in water, the mass flow ratio must be such that the atomized water can evaporate completely, leaving a solid aerosol.

It is preferred to use a pneumatic atomizer as the nebulizer. Such an atomizer allows large drops to separate from the air stream and then flow back into the atomizer. In the case of liquids which have a tendency to froth, this leads to poor operation. Therefore, in accordance with the invention, any excess liquid is removed from the atomizer unit. This trapping system according to the invention provides the enormous advantage that the concentration of the material dissolved in the aerosol always remains constant. With any liquid aerosol there is always evaporation. Therefore recycling unused aerosol has the disadvantage of changing concentrations.

Therefore, in accordance with the invention, excess liquid which collects in the atomizer is removed therefrom in such a way that it can be recovered and returned to the liquid supply container. This is achieved by providing a closed liquid circuit between the nebulizer or atomizer and the liquid supply container, so that the excess liquid can be recycled to the supply container, and no liquid is lost.

The concentration of the atomized aerosol is measured after it leaves the atomizer unit. For this purpose an aerosol sample may be diverted from the aerosol stream leaving the atomizer and conveyed to the measuring device. Alternatively, an aerosol sample to be measured may be withdrawn from the aerosol chamber. The concentration may be determined by known measuring devices, for example, by means of a light-scattering particle detector. A suitable instrument is described, for example, in German patent application No. P 41 05 190.4. The measurement device produces a signal corresponding to the value of the measured concentration. This signal is transmitted to a control computer which continuously processes and records it.

A feedback to the dosing apparatus and to the mass flow regulator also may be provided. By means of suitable software, the amount of liquid fed to the atomizer by the liquid dosing device and the amount of air fed to the atomizer and/or the dilution line by the air supply device can be adjusted by the control computer in response to the signal representing the measured aerosol concentration to achieve a desired aerosol concentration. The control computer may, if desired, be programmed so that desired aerosol concentration and air flow values can be entered into the computer prior to starting up the apparatus, and the computer will then automatically adjust the amounts of liquid and air to achieve the preset concentration and air flow values.

In accordance with a further preferred aspect of the invention, the liquid supply container, the liquid dosing device, and the mass flow controller for controlling and regulating the air stream are combined in a single apparatus, which may be referred to as a "dosing unit."

The combination of a controllable dosing unit, an aerosol concentration measuring device, and a control computer enables the aerosol generating system of the present invention to be very flexible and adaptable to a wide variety of uses and conditions. Thus, it becomes possible using the aerosol generating system of the invention to carry out any desired inhalation test protocols, i.e. the administration time and concentration of the inhaled aerosol can be preset by the operator and automatically maintained in a precise and reproducible manner. In combination with simultaneous physiological lung measurements, such as breathing volume per minute, it is possible to calculate administered dosages with high precision. Furthermore, if other physiological parameters relevant to the expected activity of the test substance are measured, either simultaneously with or before and after administration of the test substance by inhalation, it is possible to determine the physiological effect of the inhaled test substance.

In general the apparatus comprises a controllably adjustable dosing unit for providing controlled amounts of a liquid from which an aerosol is to be formed, a controllable air supply, an aerosol generator, a measuring device, preferably a photometer, for measuring the concentration of an aerosol produced in the generator, and a control unit responsive to the measuring device for adjusting the dosing unit and the air supply in order to produce an aerosol having a preset concentration.

The aerosol generator is a fluid nebulizer or atomizer comprising a control unit and a nebulizer unit. The system may be used where aerosols with adjustable concentration levels and a defined particle size distribution are required to be generated from a fluid.

The apparatus of the invention is particularly suitable for use in providing carefully controlled aerosol doses of pharmacologically active substances in experimental studies, e.g. in animal tests, but it can be used in any situation where controlled administration of an aerosol is desired, such as medical treatments.

The aerosol generator of the invention combines the following features: The generator has two air inlets, one for nebulization and one for dilution. The generator is provided with a device for measuring the volume of air which flows through the system and with a responsive control unit for adjusting the air pressure in order to regulate the amount of air flowing through the system. The generator is further provided with a device for measuring the concentration of the aerosol produced in the generator and with a responsive control unit for adjusting the amount of liquid fed to the nebulizer to regulate the concentration of the aerosol.

In accordance with a preferred embodiment, an injection port or inlet is provided through which small volumes of liquid can be injected using a normal syringe to facilitate inhalation tests when only small amounts of test substance are available.

In accordance with another preferred aspect of the invention, a timer is provided for presetting the length of time the liquid dosing pump is operated in order to control the length of the inhalation test.

In accordance with yet another preferred embodiment of the invention, the nebulizer or atomizer head is provided with a fluid outlet communicating with the liquid supply container or with an external collection vessel for removing excess liquid from the atomizer, thereby preventing generation of foam.

A preferred measurement device is an aerosol photometer which uses the principle of light scattering (diffusion) to measure the aerosol concentration over time. As long as the size distribution of the aerosol is substantially constant, the scattered light signal measured is proportional to the aerosol concentration. The photometer allows the reproducible adjustment of the nebulizer system and the monitoring of the time constancy of the aerosol concentration during the course of exposure.

To obtain absolute concentration measurements, the system must be calibrated using a filter system. This is achieved by using a weighed filter to filter all of the particles out of an aerosol after it has passed through the measurement chamber, then reweighing the filter, and subtracting the initial value from the final value to determine the weight of the liquid which was dispersed in the aerosol. By comparing the magnitude of the signal from the measuring device and the weight of the particles in the aerosol, it is possible to derive a constant which can be used to determine the absolute amount of aerosol particles measured by the photometer.

A typical photometer provides an analog measurement signal ranging from 0 to 4 volts, depending on the concentration of the aerosol sample introduced into the measurement chamber. The signal is directly proportional to the aerosol concentration and enables a direct measurement reading of the concentration of the aerosol with good time resolution.

The filter system protects the measuring device by removing from the air stream any entrained particulate matter which might damage the optical components.

The apparatus has a compact construction and is simple to operate.

The apparatus of the invention is effective in producing controlled aerosols from various types of aqueous solutions containing solutes such as proteins, amino acids, sugars, or other chemical substances. A fluid fog is generated or the solution is vaporized, depending on the proportion of the air mass flow to the fluid mass flow, and a dry aerosol of the dissolved substance remains.

By varying the pump rate, the through-flow adjustment, the compressed air unit and/or the solution concentration, fluid and solid aerosols can be adjusted to cover a wide range of concentrations. It is possible to obtain the smallest aerosol concentrations by introducing compressed air (rarefactive air) from the second compressed air outlet.

The apparatus is capable of generating extremely small dry aerosol particle sizes having average diameters of less than one-half micron (MMAD $<0.5$ $\mu$m). In certain types of experimental studies this is of great importance.

It is particularly advantageous that the apparatus of the invention makes it possible to avoid the formation of undesirable foams while producing aerosols from solutions, such as protein solutions, which tend to foam when formed into an aerosol by compressed air. This is achieved by means of the return line or outlet line through which any excess liquid which accumulates in the aerosol generator is carried away before foaming occurs. If desired, the excess liquid can be recycled to the storage reservoir of the dosing unit. This reduces the consumption of the nebulizer solution, prevents spillage, and enables the apparatus to be operated for a longer period of time on a single charge of solution.

To produce aerosols from small volumes of a solution, e.g. less than 20 ml, the solution may be injected using a conventional syringe through a diaphragm attachment connected to the inlet line. The syringe is emptied automatically by negative pressure, and the solution fed into the pump.

The aerosol concentrations in the aerosol exposure chamber are continuously or intermittently determined by the photometer, and the measured values are transmitted to the control computer and/or a printer for recording and further use, i.e. to control the liquid flow and air flow to the nebulizer.

BRIEF DESCRIPTION OF THE DRAWINGS

The invention will be explained in further detail with reference to preferred embodiments and examples illustrated in the accompanying drawings in which:

FIGS. 4(a) and 4(b) are graphs showing the aerosol particle size distribution of an example aerosol produced using the apparatus of the invention.

DETAILED DESCRIPTION OF PREFERRED EMBODIMENTS

Figure 1:
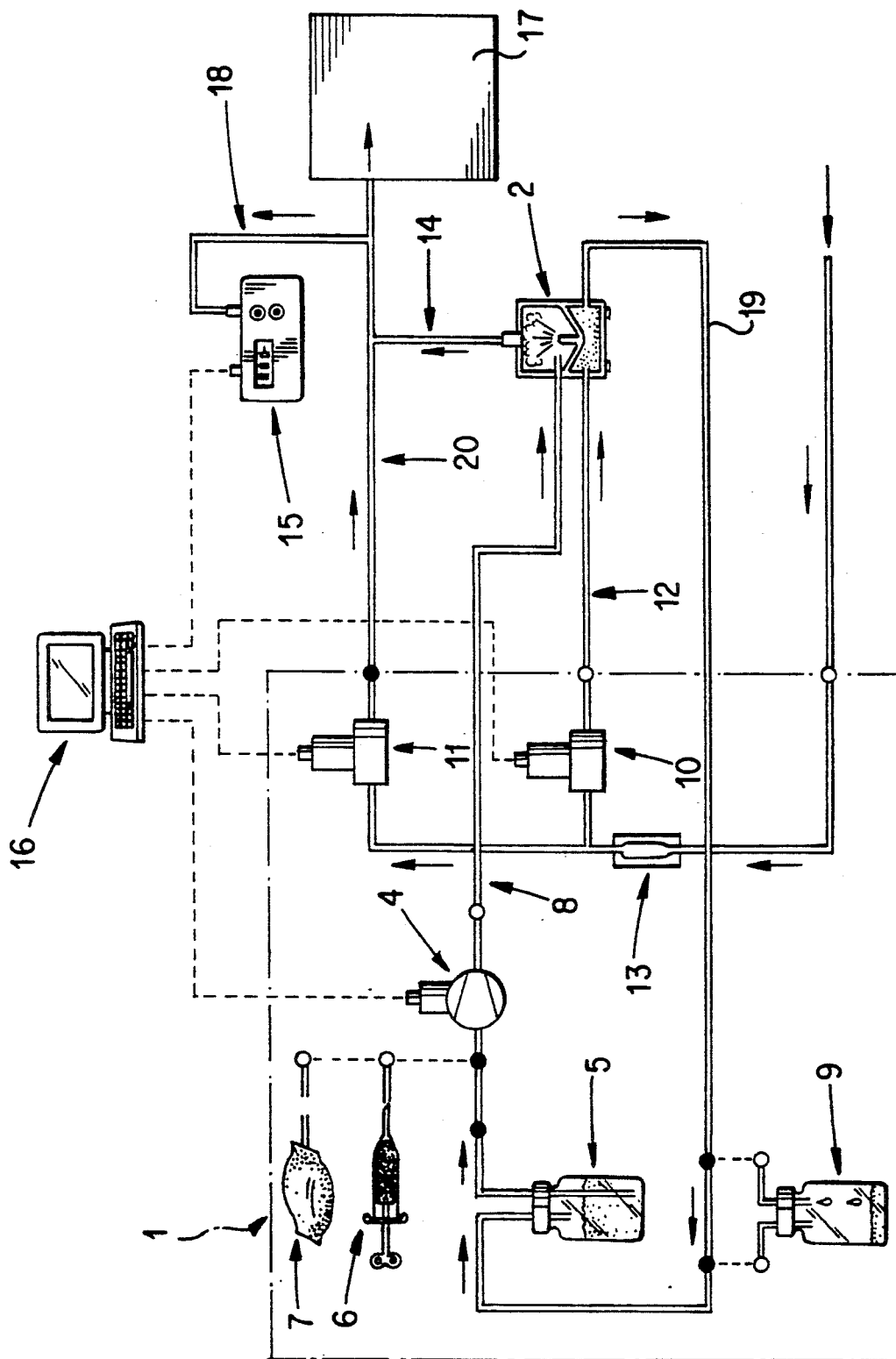
FIG. 1 is a schematic diagram of an illustrative apparatus according to the present invention.

FIG. 1 schematically depicts a preferred embodiment of the invention comprising an integrated dosing unit and illustrates the operation of the aerosol generating system of the invention. In FIG. 1, the dosing unit 1 comprises the elements enclosed within the broken line and serves several functions. The liquid is fed by the dosing pump 4, which is preferably a microdosing pump driven by a stepping motor. Pump 4 draws the desired amount of liquid either from a supply reservoir 5, a syringe 6 or a soft ampoule 7. These alternative methods of feeding the liquid assure that an appropriate liquid dosing method is provided for the desired aerosol inhalation protocol. The liquid that is supplied is then positively conveyed through the supply line 8 to the atomizer 2. Supply line 8 and return line 19 form a closed circuit so that excess liquid can be recirculated from the atomizer back into the supply reservoir 5. In an alternative embodiment, a receiver 9 is provided on return line 19 between the atomizer 2 and the supply reservoir 5 in order to collect the excess liquid and prevent it from being mingled with the fresh liquid in the supply reservoir 5 when reuse of the undispersed liquid is not desirable.

The air supply to the atomizer 2 is delivered through a duct system 12. The duct system 12 provides the atomizer 2 with the amount of air necessary to form the aerosol. A mass flow controller 10 is provided to regulate the amount of air supplied. An aerosol duct 14 carries the aerosol stream that is formed in the nebulizer to an inhalation chamber 17. Additional air can be introduced through dilution air duct 20 into aerosol duct 14 to dilute the aerosol to a desired concentration. The amount of additional air introduced through dilution air duct 20 is regulated by a second mass flow controller 11. In an advantageous configuration a filter 13 for cleaning the air is arranged in the duct system 12 upstream of the mass flow controllers 10 and 11.

In accordance with the invention, both the mass flow controllers 10 and 11 and the dosing pump 4 are controllable by means of a control computer 16 which in turn is connected to a measuring system 15, which preferably comprises a photometer. The control connections are indicated in the drawing by dashed lines. This arrangement enables the ratio between the mass flow of the liquid and the mass flow of the air in which the liquid is entrained to form an aerosol to be adjusted over a wide range, thereby making it possible to produce aerosols having different concentrations.

The atomizer 2 into which the liquid is fed through supply line 8 and the compressed air is introduced through duct system 12, is configured such that the liquid is dispersed into droplets in the air stream. Preferably, a pneumatic atomizer is used. However, pneumatic atomizers allow large droplets to separate from the air stream and flow back into the atomizer. When liquids which are prone to frothing are used, this results in poor operation. Therefore, excess liquid which collects in the atomizer 2 is removed from the atomizer by recirculating the excess liquid through return line 19.

The aerosol formed in atomizer 2 is carried by line 14 to an aerosol exposure chamber or inhalation chamber 17 or to a plethysmograph adapted to accept aerosols. The aerosol can be diluted to a desired concentration before flooding the aerosol exposure chamber by introducing a controlled amount of additional air through the dilution air duct 20.

To facilitate monitoring and control of the aerosol concentration, a sample is diverted from the aerosol duct 14 through a diversion line 18 before the aerosol stream reaches inhalation chamber 17. The volume of the diverted sample need not be large; for example, a flow of about 0.3 liters per minute is satisfactory. The diverted sample is conveyed through line 18 to a measuring device or detector 15, which forms part of the measuring and control unit and where the concentration of the aerosol is measured.

A suitable light scattering detector which can be used to measure the aerosol concentration is described, for example, in German Patent Application No. P 41 05 190. The measurement signal from detector 15 is then transmitted to a control computer 16 which continuously processes and records the signal. In accordance with a particularly preferred embodiment of the invention, a feedback to the dosing unit 1 is provided, and the control and regulating software optionally includes an automatic control program which automatically adjusts the dosing device to attain the desired preset concentration and air flow. The combination of a controllable supply unit and a control computer gives the atomizing system of the invention the capability of providing various preset aerosol dosages for predetermined time periods.

Figure 2:
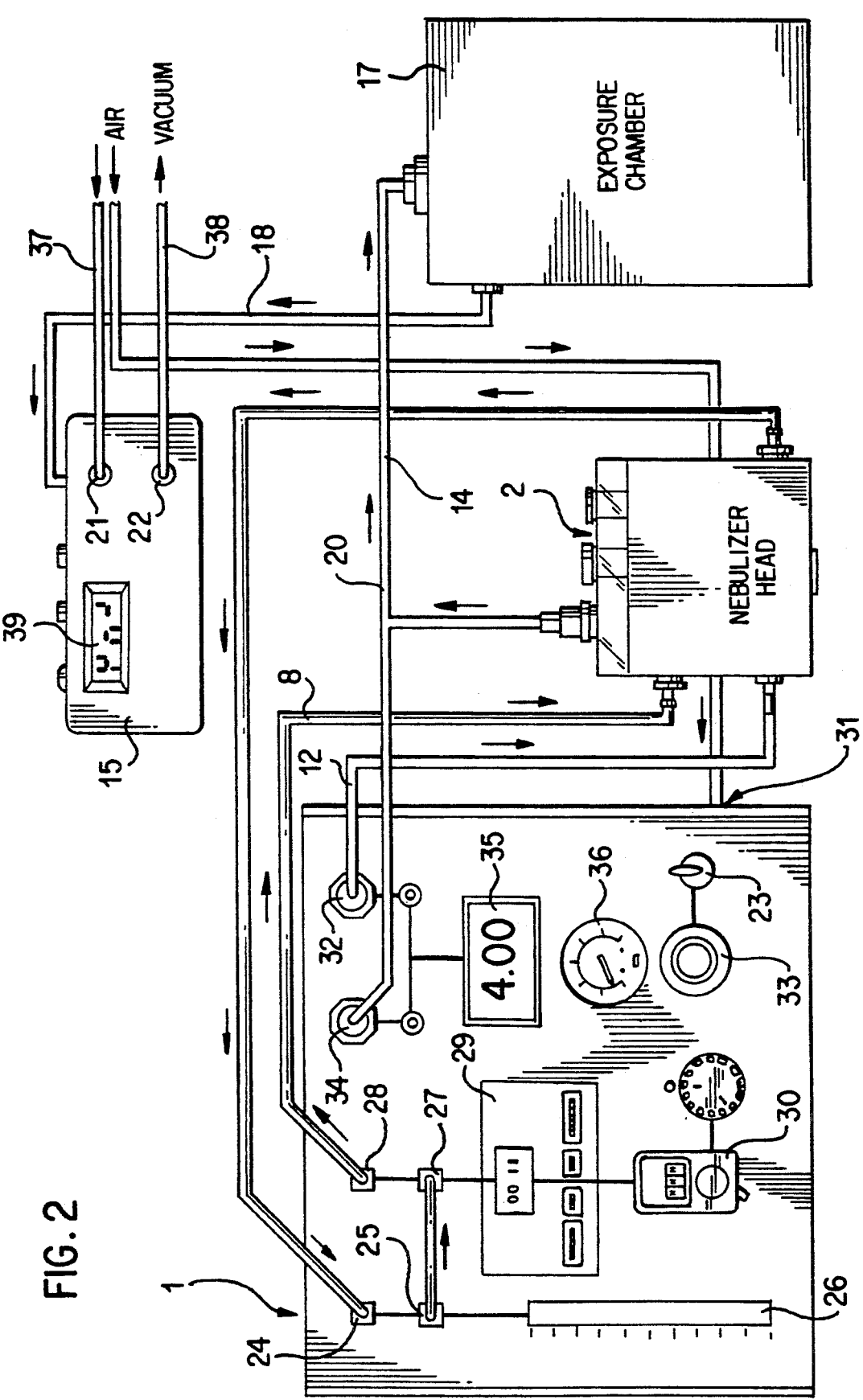
FIG. 2 is a diagrammatic view of a slightly modified apparatus according to the present invention.

FIG. 2 shows the construction of an illustrative embodiment of the inhalation system depicted in FIG. 1. In FIG. 2, the reference numbers are the same as used in the schematic diagram of FIG. 1. The microdosing pump and mass flow regulators are contained in an integrated dosing unit 1 which is connected to the atomizer 2 by air supply duct 12 and liquid supply line 8. The aerosol is conveyed from the nebulizer 2 through aerosol duct 14 to aerosol exposure chamber 17. In the embodiment of FIG. 2, the chamber 17 is connected by line 18 to the measuring device 15. The measuring device 15 also includes an air supply connection 21 and a vacuum connection 22 for establishing an air flow through the measuring device which aspirates an aerosol sample to be measured into the photometer 15 through line 18.

As shown in FIG. 2, the aerosol generator system according to the invention comprises an on/off power switch 23, a liquid supply reservoir inlet 24, a liquid supply reservoir outlet 25, a reservoir fill level indicator 26, a pump inlet 27, a pump outlet 28, a control timer 29 with an adjustment control, an adjustable pump controller 30 with a pump rate indicator and settings for manual on/off control, timer control, or computer control operation, a compressed air inlet 31, an atomizer air outlet 32, controls 33 for the compressed air mass flow regulator and dilution air mass flow regulator, a dilution air outlet 34, an air flow gauge 35, and a manometer 36 for measuring the air pressure.

In operation, the supply reservoir 5 is filled with liquid, and the reservoir outlet 25 is connected to the pump inlet 27. The pump outlet 28 and the atomizer air outlet 32 are connected to the nebulizer 2, while the dilution air outlet 34 is connected by dilution air duct 20 to the aerosol duct 14. The aerosol sampling duct 18, air supply conduit 37, and vacuum conduit 38 are also connected to the measuring device 15. The air supply should be filtered to avoid contamination of the measurement chamber or photometer optics. The power switch 23 is turned on, and the flow of compressed air is started to flush out the duct system 12, 14 and aerosol exposure chamber 17. The air flow is adjusted to the desired rate, and the respective controls are set to the desired pump rate and timer settings. After a suitable warm-up time (e.g. 30 minutes), the pump is then turned on to commence the delivery of a controlled amount of liquid to the nebulizer 2 and the formation of an aerosol therein. The aerosol passes through the duct 14 to the aerosol exposure chamber 17.

The vacuum connection on the measuring device 15 is turned on so that a sample of the aerosol is aspirated from exposure chamber 17 through line 18 to the measuring device. More air will be drawn off than through the vacuum line 38 than is supplied through the air supply line 37. The difference will be drawn in through the aerosol sampling duct 18 The concentration of the aerosol sample is measured in the measuring device 15, and the measured value (e.g. in mV) is shown on a digital display 39 and is also used by control computer 16 which is connected to the photometer output terminals to control the pump rate and the flow of compressed air and dilution air in order to maintain the desired aerosol concentration.

It is desirable to check the photometer zero point from time to time. This can be done simply by temporarily inserting an absolute filter into the aerosol sampling line. It is often sufficient to draw in clean laboratory air in comparison with the exposure concentration.

The digital display 39 of the air flow may show the total air flow, i.e. the sum of the flow of compressed air to the nebulizer and the flow of dilution air to the aerosol duct. Alternatively, separate displays can be provided for the air flow to the nebulizer and the dilution air flow.

After the desired exposure time in the aerosol chamber, the pump is turned off to stop the generation of aerosol. The flow of air is continued to flush out the ducts and exposure chamber. The pump controller rate setting is adjusted to the desired value for the next run of the test protocol, and the pump is then activated to again produce an aerosol of desired concentration for a predetermined time period. The procedure is repeated as necessary until the test protocol is completed. During each run, the pump rate and compressed air and dilution air flow rates are adjusted by computer 16 in response to the aerosol concentration value measured by the measuring device 15 as needed to maintain the desired aerosol concentration in the exposure chamber 17.

If the measured aerosol concentration values differ from each other when the air flow and pressure settings are the same, a correction can be made by slight alteration of the pump settings.

Depending on the length of exposure and the composition of the test substance, it is ordinarily desirable to disconnect the aerosol generator head after use and clean it with a suitable liquid. For aqueous solutions, it is usually sufficient to rinse the generator head with distilled water.

Figure 3:
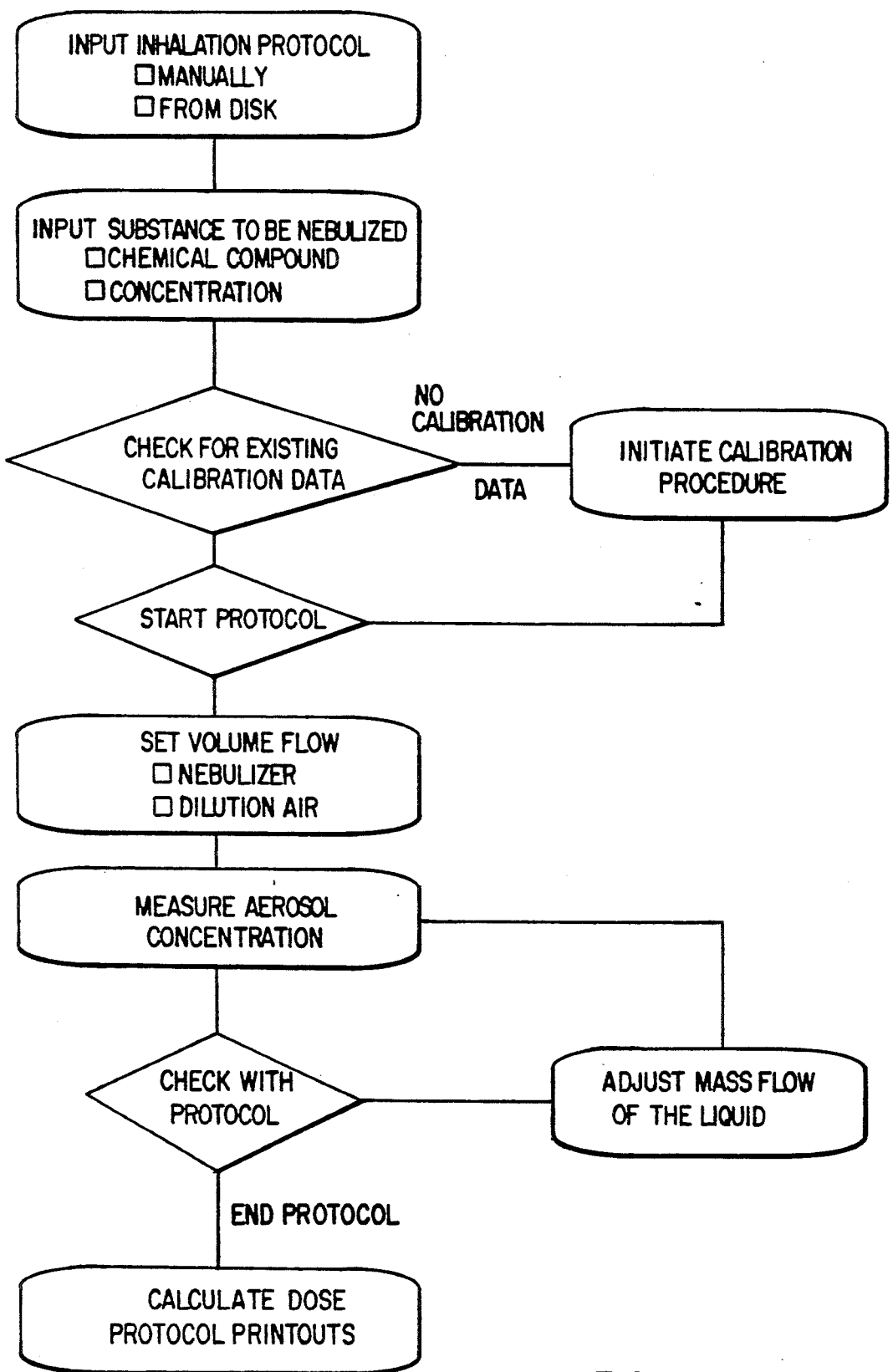
FIG. 3 is a logic diagram of a control program for the apparatus of the invention.
Figure 5:
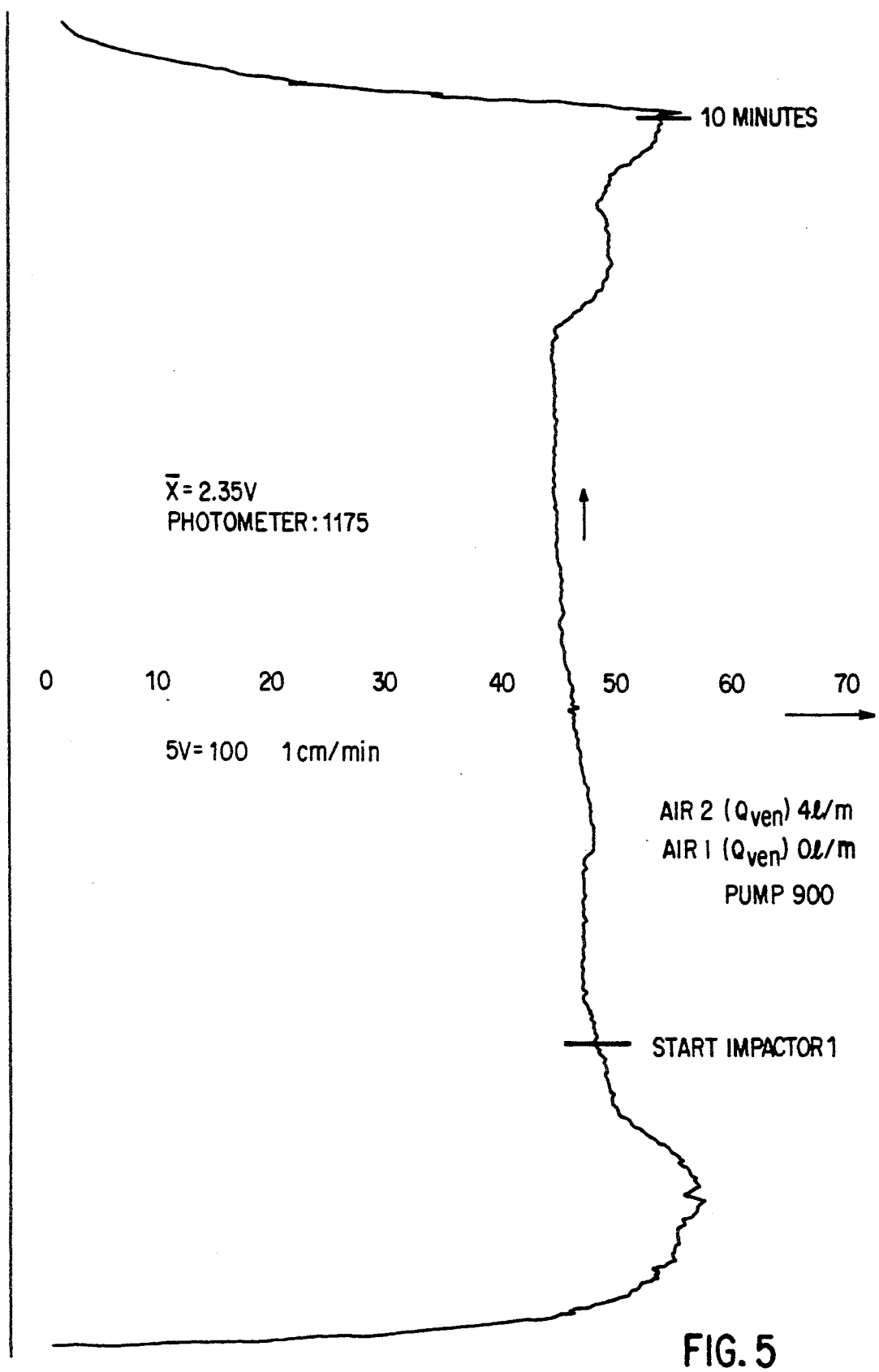
FIG. 5 is a graph of the measured concentration over time of an aerosol produced by an apparatus according to the present invention.

FIG. 3 depicts a logic diagram for a preferred control program for the apparatus of the invention. After starting, the program inquires the test protocol. The test protocol can be provided either manually as a series of "i" (i=1, 2, . . . n) inputs of exposure times, $t_i$, exposure concentrations, $c_i$ and volume flows $Q_i$, or the protocol can be selected from protocols previously stored on a magnetic disk. The program next inquires the substance (compound and concentration) to be nebulized. The program checks whether photometer calibration data already exists for the system under consideration. If not, the program will initiate the calibration procedure.

After starting the exposure, the program automatically adjusts the volume flow of the nebulizer and of the dilution air. Then it enters the feedback control loop. It measures the aerosol concentration and compares the measured value with the intended value of the protocol. Using a PID control algorithm, the program adjusts the mass flow of the liquid by adjusting the stepping motor of the pump.

At the end of the protocol, the program calculates the dose and creates graphs of the temporal concentration pattern.

Further details of the invention will become apparent from a consideration of the following examples:

EXAMPLE 1

Calibration of the Aerosol Generator

A 1% aqueous solution of ovalbumin was atomized in an aerosol generator corresponding to the apparatus of FIG. 2, except that a cascade impactor system was installed in the aerosol conduit between its junction with the dilution line and the aerosol exposure chamber. The apparatus was operated for 10 minutes with the microdosing pump at a rate of 900, while the rate of air flow to the nebulizer was 2 liters per minute. Zero dilution air was added through the dilution line. Thus the total air flow over the course of the test was 0.02 $m^3$. Fractions of the resulting aerosol were collected in the cascade impactor and weighed to yield the values shown in the following Table I:

TABLE I

| Stage No. | Size Range (microns) | Mass (mg) | % of Total Mass | Cumulative % < Cutoff | Cutoff |
|---|---|---|---|---|---|
| 9 | 21.3–30.0 | | | | 30.00 |
| 8 | 14.8–21.3 | | | | 21.30 |
| 7 | 9.8–14.8 | | | | 14.80 |
| 6 | 6.0–9.8 | | | | 9.80 |
| 5 | 3.5–6.0 | | | | 6.00 |
| 4 | 1.6–3.5 | 0.031 | 4.1 | 100.0 | 3.50 |
| 3 | 0.9–1.6 | 0.333 | 44.0 | 95.9 | 1.60 |
| 2 | 0.5–0.9 | 0.173 | 22.9 | 51.9 | 0.90 |
| 1 | 0.25–0.5 | 0.219 | 29.0 | 29.0 | 0.50 |
| Total | | 0.756 | 100.0 | | |

Dividing the total weight of the aerosol particles by the total air flow yields an aerosol concentration of 37.8 mg per $m^3$. Dividing the photometer output voltage by this value yielded a photometer calibration factor of 64.7 $mV/mg/m^3$. Since the photometer output is directly proportional to the aerosol concentration, the aerosol concentration in $mg/m^3$ for this system can be determined by dividing the output value measured by the photometer in mV by the conversion factor 64.7.

The aerosol particle size distribution curve and a logarithmic plot of the cumulative cutoff value verses the aerosol particle size in microns are shown in FIGS. 4(*a*) and 4(*b*), respectively. The mass medium aerodynamic diameter (MMAD) of the distribution is 0.72 μm. The geometric standard deviation is 1.61.

A plot made using a chart recorder (scale 5 V=100; chart speed 1 cm/min) of the photometer output in mV over the course of the test is shown in FIG. 5. The average output value X was approximately 2.35 V.

For ovalbumin (1% aqueous solution) the system generates particles with a mass medium aerodynamic diameter (MMAD) between 0.6 μm and 0.8 μm.

For acetylcholine (1% aqueous solution) particles with a MMAD between 0.5 μm and 0.8 μm are generated. An acetylcholine aerosol concentration of 1 $mg/m^3$ has been found to give a photometer output signal of 47.3 mV.

The controllable adjustability of the apparatus of the invention makes it possible to match experimental conditions created in other aerosol generating systems, so that comparable experimental data can be obtained.

EXAMPLE 2

The operation of the apparatus of the invention was demonstrated by production of aerosols of an aqueous, acetylcholine chloride-containing solution for use in an experimental animal study of bronchial hyper-reactivity induced by inhalation exposure to acetylcholine chloride.

During the running of the test, the respiratory activity of the test animals (conscious, spontaneously breathing guinea pigs) was continuously monitored in double chamber plethysmographs by the operators using the lung function measurement method of Pennock et al. (1989). The tidal volume, the respiratory rate, and the specific airway resistance of the test animal were monitored. Successively larger doses of acetylcholine chloride (ACH) were administered until the respiratory resistance increased by 100% or 200% compared to resting resistance. When a 200% increase in respiratory resistance was achieved, the provocation test was terminated. If an animal displayed strong defensive behavior, the test was discontinued before a 200% increase was achieved, to avoid endangering the animal.

The test was carried out following a provocation test protocol which called for administration of aerosols of acetylcholine chloride (ACH) at concentrations of 0.5 mg/m$^3$, 1.0 mg/m$^3$, 2.0 mg/m$^3$, 4.0 mg/m$^3$, 8.0 mg/m$^3$, 16.0 mg/m$^3$, and 32.0 mg/m$^3$. The control settings required to produce the respective aerosol concentrations are set forth in the following Table:

TABLE II

| Pump Control Setting | Timer Setting (sec) | Generator Air (l/min) | Dilution Air (l/min) | Photometer Display (mV) | Measured Concentration (mg/m$^3$) |
| --- | --- | --- | --- | --- | --- |
| 135 | 30 | 1.4 | 2.6 | 28–32 | approx. 0.5 |
| 420 | 30 | 1.4 | 2.6 | 57–64 | 1.0 |
| 60 | 30 | 2.1 | 1.9 | 115–123 | 2.0 |
| 220 | 30 | 2.1 | 1.9 | 230–250 | 4.0 |
| 560 | 30 | 2.1 | 1.9 | 470–490 | 8.0 |
| 150 | 30 | 3.4 | 0.6 | 930–990 | 16.0 |
| 360 | 30 | 4.0 | 0.0 | 1890–1950 | 32.0 |

The measuring equipment was first calibrated as described above. The test animal was then placed in the plethysmograph aerosol exposure chamber, and the respiratory activity of the test animal was measured for 1 minute at rest and continuously thereafter. After a 3 to 5 minute pause during which the aerosol generator was charged with the test solution of acetylcholine chloride and the aerosol generator was adjusted to the settings required to produce the desired 0.5 mg/m$^3$ aerosol concentration for the initial test run of the provocation test, the generator was activated to produce an aerosol for a period of 30 seconds. The system was again paused for a period of 2 minutes while the air flow and pump volume settings of the generator were adjusted to the next higher concentration for the next step of the test protocol, and the generator was then activated again for another 30 seconds. The procedure was repeated while monitoring the respiratory function of the test animal as many times as necessary until a respiratory resistance increase of 200% was achieved. The photometer display refers to a certain specific calibration. The correlation of the display to the mass concentration was checked periodically to assure consistent results.

Experience with test devices constructed according to the invention indicates that stable operation will ordinarily be achieved. However, if a baseline shift should occur in the photometer output, the apparatus can preferably be provided with a "zero adjustment" potentiometer to adjust the baseline of the photometer output to zero when only filtered air without any suspended liquid is passed through the measuring device.

Thus it can be seen that the aerosol generator of the invention serves to produce or generate controllably adjustable, reproducible aerosols of pharmaceutically active substances. The apparatus of the invention is capable of generating both dry and wet aerosols. The invention provides a universally usable, variable and easy-to-operate aerosol generator with which it is possible to carry out test protocols requiring administration of an aerosol having a predetermined concentration for a preset time in a precisely maintainable and reproducible fashion. It is particularly useful in animal tests for investigating the pharmacological activity or toxicological activity of test substances, and it removes the guesswork from aerosol dosing of groups of test animals. It enables an experimenter to perform pulmonary function tests during aerosol delivery. Use of system enables calibrated results to be obtained in different laboratories or at different times, and it facilitates comparison of data obtained in different laboratories or at different times in the same laboratory, which has not heretofore been possible. The apparatus of the invention is also applicable to aerosol dosing of humans for testing or therapeutic reasons.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An aerosol generator comprising in combination:
   a nebulizer for producing an aerosol from a liquid and an air stream;
   a device for adjustably supplying a controlled amount of a liquid from which an aerosol is to be generated to said nebulizer;
   an adjustable air source for supplying a controlled air stream to said nebulizer;
   a liquid discharge communicating with said nebulizer for discharging excess liquid from said nebulizer;
   an aerosol conduit leading from said nebulizer;
   an air flow meter for measuring the amount of air supplied by said air supply;
   a timer operatively connected to said liquid supply device and to said air source for controlling the duration of aerosol generation; and
   a detector for measuring the concentration of an aerosol discharged from said aerosol conduit.

2. An aerosol generator according to claim 1, further comprising an air filter for filtering the air supplied by said adjustable air source.

3. An aerosol generator according to claim 1, wherein said nebulizer comprises a pneumatic atomizer.

4. An aerosol generator according to claim 1, wherein said detector is a light scattering diffusion photometer.

5. An aerosol generator according to claim 1, wherein said detector is connected to said aerosol conduit by a diversion line which supplies a sample of the aerosol from said aerosol conduit to said detector for measuring the concentration of the aerosol.

6. An aerosol generator according to claim 1, wherein said liquid discharge conveys discharged excess liquid to a collection vessel.

7. An aerosol generator according to claim 1, wherein said liquid discharge communicates with a return line for recycling discharged excess liquid from said nebulizer back to said liquid supply device.

8. An aerosol generator according to claim 1, wherein said liquid supply device comprises a step dosing pump.

9. An aerosol generator according to claim 1, further comprising a recorder connected to said detector for recording the measured values of said aerosol concentration.

10. An aerosol generator according to claim 1, further comprising a control unit operatively connected to said detector and to at least one of said liquid supply device and said air source for regulating the amount of liquid supplied by said liquid supply device, the amount of air supplied by said air source, or both in response to the aerosol concentration detected by said detector in order to maintain a desired aerosol concentration.

11. An aerosol generator according to claim 1, wherein said liquid supply device comprises a syringe port for injecting a predetermined quantity of said liquid.

12. An aerosol generator according to claim 1, wherein said liquid supply device comprises means for introducing the contents of an ampoule into a carrier fluid and means for conveying said carrier fluid to said nebulizer.

13. An aerosol generator according to claim 1, wherein said adjustable air source comprises a mass flow controller.

14. An aerosol generator according to claim 1, further comprising a calibration arrangement including a filter for filtering an aerosol sample of known volume to collect the dispersed phase therefrom, and means for measuring the amount of material collected by said filter.

15. An aerosol generator according to claim 1, further comprising a dilution air line leading from said air source to said aerosol conduit, and wherein said air source supplies a second controlled air stream to said dilution air line.

16. An aerosol generator according to claim 15, wherein said air flow meter measures the total amount of air supplied to said nebulizer and to said dilution line.

17. An aerosol generator according to claim 15, further comprising a control unit operatively connected to said detector, to said liquid supply device and to said air source for regulating the amount of liquid supplied by said liquid supply device and the amount of air supplied by said air source to said nebulizer and to said dilution air line in response to the aerosol concentration detected by said detector in order to maintain a desired aerosol concentration.

18. An aerosol generator according to claim 15, wherein said air flow meter is a first air flow meter which measures the amount of air supplied to said nebulizer, and further comprising a second air flow meter for measuring the amount of air supplied to said dilution line.

19. An aerosol generator according to claim 1, further comprising an aerosol exposure chamber, and wherein said aerosol conduit discharges into said aerosol exposure chamber to convey an aerosol generated in the nebulizer to said aerosol exposure chamber.

20. An aerosol generator according to claim 19, wherein said detector is connected to said aerosol exposure chamber by a measurement sample line which supplies an aerosol sample from said aerosol exposure chamber to said detector for measuring the concentration of said aerosol.

21. An aerosol generator according to claim 19, wherein said aerosol exposure chamber is an animal exposure chamber.

* * * * *